(12) United States Patent
Brendel et al.

(10) Patent No.: US 8,044,074 B2
(45) Date of Patent: Oct. 25, 2011

(54) SUBSTITUTED HETEROCYCLES, THEIR USE AS MEDICAMENT, AND PHARMACEUTICAL PREPARATIONS COMPRISING THEM

(75) Inventors: Joachim Brendel, Bad Vilbel (DE); Heinrich Christian Englert, Frankfurt am Main (DE); Klaus Wirth, Frankfurt am Main (DE); Michael Wagner, Frankfurt am Main (DE); Jean-Marie Ruxer, Paris (FR); Fabienne Pilorge, Paris (FR)

(73) Assignee: Sanofi-Aventis, Paris (FR)

( * ) Notice: Subject to any disclaimer, the term of this patent is extended or adjusted under 35 U.S.C. 154(b) by 863 days.

(21) Appl. No.: 11/954,396

(22) Filed: Dec. 12, 2007

(65) Prior Publication Data

US 2008/0188477 A1    Aug. 7, 2008

Related U.S. Application Data

(63) Continuation of application No. PCT/EP2006/005578, filed on Jun. 10, 2006.

(30) Foreign Application Priority Data

Jun. 22, 2005  (DE) .................. 10 2005 028 862

(51) Int. Cl.
  *A61K 31/4412* (2006.01)
  *C07D 213/643* (2006.01)
(52) U.S. Cl. ......... 514/351; 514/345; 546/300; 546/301

(58) Field of Classification Search .................. 546/300, 546/301; 514/345, 351
See application file for complete search history.

(56) References Cited

U.S. PATENT DOCUMENTS

| | | |
|---|---|---|
| 7,495,014 B2 | 2/2009 | Charifson et al. |
| 7,569,591 B2 | 8/2009 | Charifson et al. |
| 2004/0235886 A1 | 11/2004 | Charifson et al. |
| 2005/0038247 A1 | 2/2005 | Charifson et al. |
| 2005/0054673 A1 | 3/2005 | Wirth |
| 2007/0027177 A1 | 2/2007 | Trotter et al. |

FOREIGN PATENT DOCUMENTS

WO   WO 2005-046578   5/2005

*Primary Examiner* — Patricia Morris
(74) *Attorney, Agent, or Firm* — Kelly L. Bender; Ronald G. Ort

(57) ABSTRACT

The invention relates to compounds of formula I

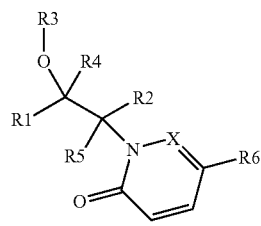

in which R1, R2, R3, R4, R5, R6 and X have the meanings stated in the claims. The compounds are particularly suitable as antiarrhythmic active ingredients, in particular for the treatment and prophylaxis of atrial arrhythmias, for example atrial fibrillation (AF) or atrial flutter.

6 Claims, No Drawings

SUBSTITUTED HETEROCYCLES, THEIR USE AS MEDICAMENT, AND PHARMACEUTICAL PREPARATIONS COMPRISING THEM

FIELD OF THE INVENTION

The invention relates to compounds of formula I,

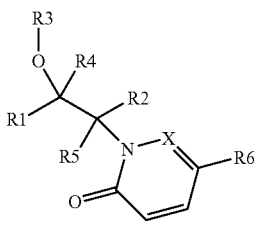

in which R1, R2, R3, R4, R5, R6 and X have the meanings stated below, to their preparation and their use, in particular in pharmaceuticals.

BACKGROUND OF THE INVENTION

The compounds of the invention of formula I have not previously been described. They act on the so-called Kv1.5 potassium channel and inhibit a potassium current which is designated the ultra-rapidly activating delayed rectifier in the human atrium. In addition, the compounds also act on other atrium-specific potassium channels such as the acetylcholine-dependent potassium channel KACh, and the 2P domain potassium channel TASK-1. The compounds are therefore very particularly suitable as antiarrhythmic active ingredients, in particular for the treatment and prophylaxis of atrial arrhythmias, for example atrial fibrillation (AF) or atrial flutter.

Atrial fibrillation (AF) and atrial flutter are the commonest sustained cardiac arrhythmias. The incidence increases with increasing age and frequently leads to fatal sequelae such as, for example, stroke. AF affects for example about 3 million Americans and leads to more than 80 000 strokes each year in the USA. Although class I and III antiarrhythmics currently in use can reduce the rate of recurrence of AF, their use is restricted owing to their potential proarrhythmic side effects. There is for this reason a great medical need for better medicaments for treating atrial arrhythmias to be developed.

It has been shown that so-called reentry depolarization waves underlie most supraventricular arrhythmias. Such reentries occur if the cardiac tissue has a slow conductivity and, at the same time, very short refractory periods. The increase in the myocardial refractory period by prolonging the action potential is an accepted mechanism for terminating arrhythmias and preventing their development. The length of the action potential is substantially determined by the extent of repolarizing $K^+$ currents which flow out of the cell through the various $K^+$ channels. Particularly great importance is ascribed in this connection to the so-called delayed rectifier $I_K$ which consists of 3 different components: $IK_r$, $IK_s$ and $IK_{ur}$.

Most known class III antiarrhythmics (for example dofetilide or d-sotalol) block predominantly or exclusively the rapidly activating potassium channel $IK_r$ which has been detected both in cells of the human ventricle and in the atrium. However, it has emerged that these compounds have an increased proarrhythmic risk when heart rates are low or normal, and the arrhythmias which have been observed are in particular those referred to as torsades de pointes. Besides this high risk, which is fatal in some cases, when the rate is low, the efficacy of $IK_r$ blockers has been found to decline under the conditions of tachycardia, which is just when the effect is required ("negative use-dependence").

The "particularly rapidly" activating and very slowly inactivating component of the delayed rectifier $IK_{ur}$ (=ultra-rapidly activating delayed rectifier), which corresponds to the Kv1.5 channel, is of particularly great importance for the duration of repolarization in the human atrium. Inhibition of the $IK_{ur}$ potassium outward current thus represents, by comparison with inhibition of $IK_r$ or $IK_s$, a particularly effective method for prolonging the atrial action potential and thus for terminating or preventing atrial arrhythmias. Mathematical models of the human action potential suggest that the positive effect of a blockade of the $IK_{ur}$ ought to be particularly pronounced precisely under the pathological conditions of chronic atrial fibrillation (M. Courtemanche, R. J. Ramirez, S, Nattel, Cardiovascular Research 1999, 42, 477-489: "Ionic targets for drug therapy and atrial fibrillation-induced electrical remodeling: insights from a mathematical model").

In contrast to $IK_r$ and $IK_s$, which also occur in the human ventricle, $IK_{ur}$ plays a significant role in the human atrium, but not in the ventricle. For this reason, if the $IK_{ur}$ current is inhibited, the risk of a proarrhythmic effect on the ventricle is precluded from the outset, in contrast to blockade of $IK_r$ or $IK_s$ (Z. Wang et al, Circ. Res. 73, 1993, 1061-1076: "Sustained Depolarisation-Induced Outward Current in Human Atrial Myocytes"; G.-R. Li et al, Circ. Res. 78, 1996, 689-696: "Evidence for Two Components of Delayed Rectifier $K^+$-Current in Human Ventricular Myocytes"; G. J. Amos et al, J. Physiol. 491, 1996, 31-50: "Differences between outward currents of human atrial and subepicardial ventricular myocytes").

Antiarrhythmics which act by atrium-selective blockade of the $IK_{ur}$ current or Kv1.5 channel have not, however, been available on the market to date. Although a blocking effect on the Kv1.5 channel has been described for numerous active pharmaceutical ingredients (for example quinidine, bupivacaine or propafenone), the Kv1.5 blockade in each of these cases represents only a side effect in addition to other main effects of the substances.

A number of patent applications in recent years have described various substances as Kv1.5 channel blockers. A compilation and detailed discussion of these substances has recently been published (J. Brendel, S. Peukert; Curr. Med. Chem.—Cardiovascular & Hematological Agents, 2003, I, 273-287; "Blockers of the Kv1.5 Channel for the Treatment of Atrial Arrhythmias"). However, all Kv1.5 blockers disclosed to date and described therein have entirely different types of structures than the compounds of the invention in this application. In addition, no clinical data on the effect and tolerability in humans have been disclosed to date for any of the compounds disclosed to date. Since experience has shown that only a small proportion of active ingredients successfully overcome all the clinical hurdles from preclinical research to the medicament, there continues to be a need for novel, promising substances.

SUMMARY OF THE INVENTION

It has now been found, surprisingly, that the compounds of the invention of formula I and/or their pharmaceutically acceptable salts are potent blockers of the human Kv1.5 channel.

In addition, the compounds of formula I and/or their pharmaceutically acceptable salts also act on the acetylcholine-activated potassium channel KACh and on the TASK-1 channel, which likewise predominantly occur in the atrium (Krapivinsky G., Gordon E. A., Wickman K., Velimirovic B., Krapivinsky L., Clapham D. E.: "The G-protein-gated atrial K$^+$ channel I$_{KACh}$ is a heteromultimer of two inwardly rectifying K$^+$-channel proteins", Nature 374 (1995) 135-141; Liu, W., Saint, D. A.: "Heterogeneous expression of tandem-pore K$^+$ channel genes in adult and embryonic rat heart quantified by real-time polymerase chain reaction", Clin. Exp. Pharmacol. Physiol. 31 (2004) 174-178; Jones S. A., Morton, M. J., Hunter M., Boyett M. R.: "Expression of TASK-1, a pH-sensitive twin-pore domain K$^+$ channel, in rat myocytes", Am. J. Physiol. 283 (2002) H181-H185).

Because of this combined effect on a plurality of atrium-specific potassium channels, the compounds of formula I and/or their pharmaceutically acceptable salts can therefore be used as novel antiarrhythmics with a particularly advantageous safety profile. The compounds are suitable in particular for the treatment of supraventricular arrhythmias, for example atrial fibrillation or atrial flutter.

The compounds of formula I and/or pharmaceutically acceptable salts thereof can also be employed for the treatment and prevention of diseases where the atrium-specific potassium channels, for example the Kv1.5, the KACh and/or the TASK-1, are only partially inhibited, for example by using a lower dosage.

The compounds of formula I and/or their pharmaceutically acceptable salts can be employed to produce medicaments with a K$^+$ channel-blocking effect for the therapy and prophylaxis of K$^+$ channel-mediated diseases. The compounds of formula I and/or their pharmaceutically acceptable salts can further be used for the therapy or prophylaxis of cardiac arrhythmias which can be abolished by prolonging the action potential.

The compounds of formula I and/or their pharmaceutically acceptable salts can be employed for terminating existent atrial fibrillation or flutter to restore the sinus rhythm (cardioversion). In addition, the substances reduce the susceptibility to the development of new fibrillation events (maintenance of sinus rhythm, prophylaxis). It has further been observed that the substances are effective for preventing life-threatening ventricular arrhythmias (ventricular fibrillation) and are able to protect from sudden heart death without, however, simultaneously bringing about an unwanted prolongation of the so-called QT interval.

The compounds of formula I and/or their pharmaceutically acceptable salts can be employed for producing a medicament for the therapy or prophylaxis of reentry arrhythmias, of supraventricular arrhythmias, atrial fibrillation and/or atrial flutter.

The compounds of formula I and/or their pharmaceutically acceptable salts are further suitable for producing a medicament for the therapy or prophylaxis of heart failure, in particular of diastolic heart failure and for increasing atrial contractility.

The compounds of formula I and/or pharmaceutically acceptable salts thereof inhibit TASK potassium channels, for example the subtypes TASK-1 and TASK-3, in particular the subtype TASK-1. Because of the TASK-inhibitory properties, the compounds of formula I and/or their pharmaceutically acceptable salts are suitable for the prevention and treatment of diseases caused by activation or by an activated TASK-1, and of diseases caused secondarily by the TASK-1-related damage.

Because of the effect of the substances on the TASK channel, the compounds of formula I and/or their pharmaceutically acceptable salts are also suitable for producing a medicament for the therapy or prophylaxis of respiratory disorders, especially sleep apneas, neurodegenerative disorders and cancers, for example sleep-related respiratory disorders, central and obstructive sleep apneas, Cheyne-Stoke's breathing, snoring, impaired central respiratory drive, sudden infant death, postoperative hypoxia and apnea, muscle-related respiratory disorders, respiratory disorders following long-term ventilation, respiratory disorders associated with altitude adaptation, acute and chronic pulmonary disorders with hypoxia and hypercapnia, neurodegenerative disorders, dementia, Alzheimer's disease, Parkinson's disease, Huntington's disease, cancers, breast cancer, lung cancer, colon cancer and prostate cancer.

DETAILED DESCRIPTION OF THE INVENTION

The present invention relates to compounds of formula I

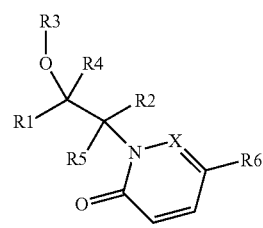

in which the meanings are:
R1 phenyl, pyridyl, thienyl, naphthyl, quinolinyl, pyrimidinyl or pyrazinyl,
  where each of these aryl radicals is unsubstituted or substituted by 1, 2 or 3 substituents selected from the group consisting of F, Cl, Br, I, CN, alkoxy having 1, 2, 3 or 4 carbon atoms, OCF$_3$, methylsulfonyl, CF$_3$, alkyl having 1, 2, 3 or 4 carbon atoms, dimethylamino, sulfamoyl, acetyl, and methylsulfonylamino;
R2 phenyl, pyridyl, thienyl, naphthyl, quinolinyl, pyrimidinyl or pyrazinyl,
  where each of these aryl radicals is unsubstituted or substituted by 1, 2 or 3 substituents selected from the group consisting of F, Cl, Br, I, CN, COOMe, CONH$_2$, alkoxy having 1, 2, 3 or 4 carbon atoms, OCF$_3$, OH, methylsulfonyl, CF$_3$, alkyl having 1, 2, 3 or 4 carbon atoms, dimethylamino, sulfamoyl, acetyl, and methylsulfonylamino;
R3 C$_p$H$_{2p}$—R7;
  p 0, 1, 2, 3, 4 or 5;
  R7 CH$_3$, CH$_2$F, CHF$_2$, CF$_3$, cycloalkyl having 3, 4, 5, 6 or 7 carbon atoms, C≡CH, C≡C—CH$_3$, alkoxy having 1, 2, 3 or 4 carbon atoms, phenyl or 2-pyridyl,
    where phenyl and pyridyl are unsubstituted or substituted by 1, 2 or 3 substituents selected from the group consisting of F, Cl, Br, I, CF$_3$, OCF$_3$, CN, COOMe, CONH$_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R4 hydrogen or alkyl having 1, 2 or 3 carbon atoms;
R5 hydrogen or alkyl having 1, 2 or 3 carbon atoms;
R6 hydrogen, F, Cl, CF$_3$ or alkyl having 1, 2 or 3 carbon atoms;

X CH or N;

and the pharmaceutically acceptable salts and trifluoroacetates thereof.

Particularly preferred compounds of formula I are those in which the meanings are:

R1 phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl, 8-quinolinyl, 2-pyrimidinyl, 4-pyrimidinyl, 5-pyrimidinyl, 2-pyrazinyl, 3-pyridazinyl or 4-pyridazinyl,
  where each of these aryl radicals is unsubstituted or substituted by 1, 2 or 3 substituents selected from the group consisting of F, Cl, Br, I, CN, alkoxy having 1, 2, 3 or 4 carbon atoms, $OCF_3$, methylsulfonyl, $CF_3$, alkyl having 1, 2, 3 or 4 carbon atoms, dimethylamino, sulfamoyl, acetyl, and methylsulfonylamino;

R2 phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl, 8-quinolinyl, 2-pyrimidinyl, 4-pyrimidinyl, 5-pyrimidinyl, 2-pyrazinyl, 3-pyridazinyl or 4-pyridazinyl,
  where each of these aryl radicals is unsubstituted or substituted by 1, 2 or 3 substituents selected from the group consisting of F, Cl, Br, I, CN, COOMe, $CONH_2$, alkoxy having 1, 2, 3 or 4 carbon atoms, $OCF_3$, OH, methylsulfonyl, $CF_3$, alkyl having 1, 2, 3 or 4 carbon atoms, dimethylamino, sulfamoyl, acetyl, and methylsulfonylamino;

R3 $C_pH_{2p}$—R;
  p 0, 1, 2, 3, 4 or 5;
  R7 $CH_3$, $CH_2F$, $CHF_2$, $CF_3$, cycloalkyl having 3, 4, 5, 6 or 7 carbon atoms, C≡CH, C≡C—$CH_3$, alkoxy having 1, 2, 3 or 4 carbon atoms, phenyl or 2-pyridyl,
    where phenyl and 2-pyridyl are unsubstituted or substituted by 1, 2 or 3 substituents selected from the group consisting of F, Cl, Br, I, $CF_3$, $OCF_3$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R4 hydrogen or alkyl having 1, 2 or 3 carbon atoms;
R5 hydrogen or alkyl having 1, 2 or 3 carbon atoms;
R6 hydrogen, F, Cl, $CF_3$ or alkyl having 1, 2 or 3 carbon atoms;
X CH or N;

and the pharmaceutically acceptable salts and trifluoroacetates thereof.

Compounds of formula I preferred in one embodiment are those in which the meanings are:

R1 phenyl
  which is unsubstituted or substituted by 1, 2 or 3 substituents selected from the group consisting of F, Cl, Br, I, CN, alkoxy having 1, 2, 3 or 4 carbon atoms, $OCF_3$, methylsulfonyl, $CF_3$, alkyl having 1, 2, 3 or 4 carbon atoms, dimethylamino, sulfamoyl, acetyl, and methylsulfonylamino;

R2 phenyl,
  which is unsubstituted or substituted by 1, 2 or 3 substituents selected from the group consisting of F, Cl, Br, I, CN, COOMe, $CONH_2$, alkoxy having 1, 2, 3 or 4 carbon atoms, $OCF_3$, OH, methylsulfonyl, $CF_3$, alkyl having 1, 2, 3 or 4 carbon atoms, dimethylamino, sulfamoyl, acetyl, and methylsulfonylamino;

R3 $C_pH_{2p}$—R7;
  p 0, 1, 2, 3, 4 or 5;
  R7 $CH_3$, $CH_2F$, $CHF_2$, $CF_3$, cycloalkyl having 3, 4, 5, 6 or 7 carbon atoms, C≡CH, C≡C—$CH_3$, alkoxy having 1, 2, 3 or 4 carbon atoms, phenyl or 2-pyridyl,
    where phenyl and 2-pyridyl are unsubstituted or substituted by 1, 2 or 3 substituents selected from the group consisting of F, Cl, Br, I, $CF_3$, $OCF_3$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;

R4 hydrogen;
R5 hydrogen;
R6 hydrogen, F or alkyl having 1, 2, or 3 carbon atoms;
X CH or N;

and the pharmaceutically acceptable salts and trifluoroacetates thereof.

Compounds of formula I particularly preferred in one embodiment are those in which the meanings are:

R1 phenyl,
  which is unsubstituted or substituted by 1 substituent from the group consisting of F, Cl, Br, I, CN and alkoxy having 1 or 2 carbon atoms;

R2 phenyl,
  which is unsubstituted or substituted by 1 substituent from the group consisting of F, Cl, Br, I, CN and alkoxy having 1 or 2 carbon atoms;

R3 $C_pH_{2p}$—R7;
  p 0, 1, 2, 3;
  R7 $CH_3$, cycloalkyl having 3 or 4 carbon atoms or phenyl where phenyl is unsubstituted or substituted by 1 or 2 substituents selected from the group consisting of F, Cl, Br, I, CN, alkyl having 1 or 2 carbon atoms and alkoxy having 1 or 2 carbon atoms;

R4 hydrogen;
R5 hydrogen;
R6 hydrogen, F or alkyl having 1 or 2 carbon atoms;
X CH or N;

and the pharmaceutically acceptable salts and trifluoroacetates thereof.

Compounds of formula I very particularly preferred in one embodiment are those in which the meanings are:

R1 phenyl,
  which is unsubstituted or substituted by one substituent from the group consisting of F, Cl, Br, I, CN and alkoxy having 1 or 2 carbon atoms;

R2 phenyl,
  which is unsubstituted or substituted by one substituent from the group consisting of F, Cl, Br, I, CN and alkoxy having 1 or 2 carbon atoms;

R3 $C_pH_{2p}$—R7;
  p 0, 1, 2 or 3;
  R7 $CH_3$, cycloalkyl having 3 or 4 carbon atoms or phenyl, where phenyl is unsubstituted or substituted by 1 or 2 substituents selected from the group consisting of F, Cl, Br, CN, alkyl having 1 or 2 carbon atoms and alkoxy having 1 or 2 carbon atoms;

R4 hydrogen;
R5 hydrogen;
R6 hydrogen, F or alkyl having 1 or 2 carbon atoms;
X N;

and the pharmaceutically acceptable salts and trifluoroacetates thereof.

Specifically preferred compounds of formula I are selected from the group
1R',2R'-1-(2-Cyclopropylmethoxy-1,2-diphenylethyl)-1H-pyridin-2-one, 1R',2S'-1-[2-Cyclopropylmethoxy-1-(4-fluorophenyl)-2-(4-methoxyphenyl)ethyl]-1H-pyridin-2-one,
1-(2-Cyclopropylmethoxy-1,2-diphenylethyl)-5-fluoro-1H-pyridin-2-one,
2-[2-(4-Chlorophenyl)-2-cyclopropylmethoxy-1-phenyl-ethyl]-2H-pyridazin-3-one,
1R',2R'-5-Fluoro-1-(2-p-cyanophenoxy-1,2-di-p-fluorophenylethyl)-1H-pyridin-2-one,
1-[2-Cyclopropoxy-1,2-bis(4-fluorophenyl)ethyl]-5-fluoro-1H-pyridin-2-one,
1-[2-(4-Chlorophenyl)-2-cyclopropylmethoxy-1-phenyl-ethyl]-1H-pyridin-2-one,
1R',2R'-1-[2-Cyclopropylmethoxy-1,2-bis(4-fluorophenyl)ethyl]-1H-pyridin-2-one,
1R',2S'-1-[2-Cyclopropylmethoxy-1,2-bis-(4-fluorophenyl)ethyl]-1H-pyridin-2-one,
1-[2-(4-Bromophenyl)-2-cyclopropylmethoxy-1-(4-fluorophenyl)ethyl]-1H-pyridin-2-one,
4-[1-Cyclopropylmethoxy-2-(4-fluorophenyl)-2-(2-oxo-2H-pyridin-1-yl)ethyl]benzonitrile,
1R',2R'-1-(2-Cyclopropylmethoxy-1,2-diphenylethyl)-5-fluoro-1H-pyridin-2-one,
1R',2R'-1-[1-(4-Fluorophenyl)-2-(4-methoxybenzyloxy)-2-(4-methoxyphenyl)ethyl]-1H-pyridin-2-one,
1-[2-Cyclopropylmethoxy-1,2-bis-(4-fluorophenyl)ethyl]-1H-pyridin-2-one,
4-[1-(4-Chlorophenyl)-2-(2-oxo-2H-pyridin-1-yl)-2-phenylethoxymethyl]benzonitrile,
1-[2-Cyclopropylmethoxy-1,2-bis-(4-fluorophenyl)ethyl]-5-fluoro-1H-pyridin-2-one,
1R',2R'-1-[2-Cyclopropylmethoxy-1-(4-fluorophenyl)-2-(4-methoxyphenyl)ethyl]-1H-pyridin-2-one
and
1R',2S'-1-[1-(4-Fluorophenyl)-2-(4-methoxybenzyloxy)-2-(4-methoxyphenyl)ethyl]-1H-pyridin-2-one,
and the pharmaceutically acceptable salts and trifluoroacetates thereof.

One embodiment describes compounds of formula I in which R1 is phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl, 8-quinolinyl, 2-pyrimidinyl, 4-pyrimidinyl, 5-pyrimidinyl, 2-pyrazinyl, 3-pyridazinyl or 4-pyridazinyl, in particular phenyl, where each of these aryl radicals is unsubstituted or substituted by 1, 2 or 3 substituents selected from the group consisting of F, Cl, Br, I, CN, alkoxy having 1, 2, 3 or 4 carbon atoms, $OCF_3$, methylsulfonyl, $CF_3$, alkyl having 1, 2, 3 or 4 carbon atoms, dimethylamino, sulfamoyl, acetyl, and methylsulfonylamino, preferably selected from the group consisting of F, Cl, Br, I, CN and alkoxy having 1 or 2 carbon atoms, for example F, Cl, Br, CN or methoxy.

A further embodiment describes compounds of formula I in which R2 is phenyl, 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl, 8-quinolinyl, 2-pyrimidinyl, 4-pyrimidinyl, 5-pyrimidinyl, 2-pyrazinyl, 3-pyridazinyl or 4-pyridazinyl, in particular phenyl, where each of these aryl radicals is unsubstituted or substituted by 1, 2 or 3 substituents selected from the group consisting of F, Cl, Br, I, CN, alkoxy having 1, 2, 3 or 4 carbon atoms, $OCF_3$, methylsulfonyl, $CF_3$, alkyl having 1, 2, 3 or 4 carbon atoms, dimethylamino, sulfamoyl, acetyl, and methylsulfonylamino, preferably selected from the group consisting of F, Cl, Br, I, CN, $CF_3$ and alkoxy having 1 or 2 carbon atoms, for example F.

A further embodiment describes compounds of formula I in which R3 is $C_pH_{2p}$—R7, where p is 0, 1, 2 or 3, in particular 0 or 1, for example 1, and R7 is $CH_3$, cycloalkyl having 3 or 4 carbon atoms or phenyl, for example cyclopropyl or phenyl, where phenyl is unsubstituted or substituted by 1 or 2 substituents selected from the group consisting of F, Cl, Br, CN, alkyl having 1 or 2 carbon atoms and alkoxy having 1 or 2 carbon atoms, for example selected from the group consisting of methoxy and CN.

A further embodiment describes compounds of formula I in which R4 is hydrogen or methyl, for example hydrogen.

A further embodiment describes compounds of formula I in which R5 is hydrogen or methyl, for example hydrogen.

A further embodiment describes compounds of formula I in which R6 is hydrogen, F or alkyl having 1 or 2 carbon atoms, for example hydrogen or fluorine.

A further embodiment describes compounds of formula I in which X is CH.

A further embodiment describes compounds of formula I in which X is N.

The compounds of formula I may exist in stereoisomeric forms. The centers of asymmetry which are present may independently of one another have the S configuration or the R configuration. The invention includes all possible stereoisomers, for example enantiomers or diastereomers, and mixtures of two or more stereoisomeric forms, for example enantiomers and/or diastereomers, in any ratios. The invention thus includes for example enantiomers in enantiopure form, both as levorotatory and as dextrorotatory antipodes, and in the form of mixtures of the two enantiomers in various ratios or in the form of racemates. Individual stereoisomers can be prepared as desired by fractionating a mixture by conventional methods or for example by stereoselective synthesis.

If mobile hydrogen atoms are present, the present invention also includes all tautomeric forms of compounds of formula I.

The present invention further includes derivatives of compounds of formula I, for example solvates, such as hydrates and alcohol adducts, esters, prodrugs and other physiologically acceptable derivatives of the compounds of formula I, and active metabolites of the compounds of formula I. The invention likewise includes all crystal modifications of the compounds of formula I.

Alkyl radicals and alkylene radicals may be straight-chain or branched. This also applies to the alkylene radicals of formula $C_pH_{2p}$. Alkyl radicals and alkylene radicals may also be straight-chain or branched if they are substituted or are present in other radicals, for example in an alkoxy radical or in a fluorinated alkyl radical. Examples of alkyl radicals are methyl, ethyl, n-propyl, isopropyl, n-butyl, isobutyl, sec-butyl and tert-butyl. The divalent radicals derived from these radicals, for example methylene, 1,1-ethylene, 1,2-ethylene, 1,1-propylene, 1,2-propylene, 2,2-propylene, 1,3-propylene, 1,1-butylene, 1,4-butylene, etc. are examples of alkylene radicals. One or more, for example 1, 2, 3, 4, 5, 6, 7, 8, or 9 hydrogen atoms in alkyl and alkylene radicals may be replaced by fluorine atoms. Substituted alkyl radicals may be substituted in any positions.

Cycloalkyl radicals may likewise be branched. Examples of cycloalkyl radicals having 3 to 7 carbon atoms are cyclopropyl, cyclobutyl, 1-methylcyclopropyl, 2-methylcyclopropyl, cyclopentyl, 2-methylcyclobutyl, 3-methylcyclobutyl, cyclopentyl, cyclohexyl, 2-methylcyclohexyl, 3-methylcyclohexyl, 4-methylcyclohexyl, cycloheptyl etc. One or more, for example 1, 2, 3, 4, 5, 6, 7, 8, 9, 10, 11, 12, 13 or 14 hydrogen atoms in cycloalkyl radicals may be replaced by fluorine atoms. Substituted cycloalkyl radicals may be substituted in any positions. Cycloalkyl radicals may also be in branched form as alkylcycloalkyl or cycloalkylalkyl, for example methylcyclohexyl or cyclohexylmethyl.

Phenyl radicals may be unsubstituted or substituted one or more times, for example once, twice or three times, by identical or different radicals. If a phenyl radical is substituted, it preferably has one or two identical or different substituents. Monosubstituted phenyl radicals may be substituted in position 2, 3 or 4, disubstituted in 2,3-, 2,4-, 2,5-, 2,6-, 3,4- or 3,5-, position trisubstituted in 2,3,4-, 2,3,5-, 2,3,6-, 2,4,5-, 2,4,6- or 3,4,5-position. A corresponding statement applies analogously also to the N-containing heteroaromatic systems such as pyridyl, quinolinyl, pyrimidinyl or pyrazinyl, the naphthyl radical and the thienyl radical, for example for 2-pyridyl, 3-pyridyl, 4-pyridyl, 2-thienyl, 3-thienyl, 1-naphthyl, 2-naphthyl, 2-quinolinyl, 3-quinolinyl, 4-quinolinyl, 5-quinolinyl, 6-quinolinyl, 7-quinolinyl, 8-quinolinyl, 2-pyrimidinyl, 4-pyrimidinyl, 5-pyrimidinyl, 2-pyrazinyl, 3-pyridazinyl or 4-pyridazinyl.

If a radical is di- or trisubstituted, the substituents may be identical or different.

If the compounds of formula I comprise one or more basic groups or one or more basic heterocycles, the invention also includes the corresponding physiologically, pharmaceutically or toxicologically acceptable salts, especially the pharmaceutically acceptable salts, but also the trifluoroacetates. Thus, the compounds of formula I which have one or more basic, i.e. protonatable, groups or comprise one or more basic heterocyclic rings, can also be used in the form of their physiologically tolerated acid addition salts with inorganic or organic acids, for example as hydrochlorides, phosphates, sulfates, methanesulfonates, acetates, lactates, maleates, fumarates, malates, gluconates etc. Salts can be obtained from compounds of formula I by conventional processes, for example by combining with an acid in a solvent or dispersant or else by anion exchange from other salts. The compounds of formula I may also be deprotonated on an acidic group and be used for example as alkali metal salts, preferably sodium or potassium salts, or as ammonium salts, for example as salts with ammonia or organic amines or amino acids.

The invention further relates to processes for preparing the compounds of formula I.

The compounds of formula I can be prepared by various chemical processes, where R1, R2, R3, R4, R5, R6 and X have the same meaning as in compounds of formula I.

The preparation takes place for example according to scheme 1 by N-alkylation of R6-substituted 2-hydroxypyridines or 3-hydroxypyridazines of formula III with 2-bromo ketones of formula II with subsequent reduction of the keto function to compounds of formula Va. The compounds of formula Va are then reacted by standard processes with compounds of formula VI to give the corresponding compounds of formula Ia, where X1 has the meaning of an appropriate leaving group, for example a halide such as chloride, bromide or iodide or else tosylate.

Scheme 1

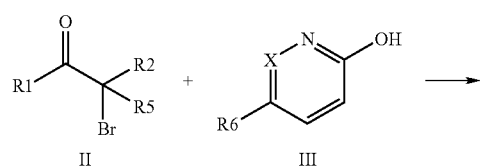

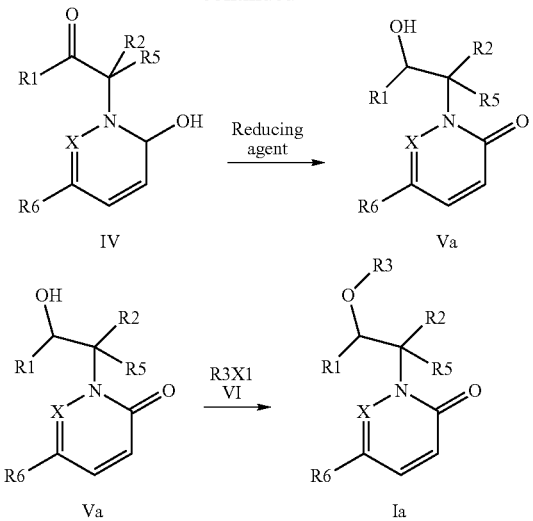

A further preparation process is depicted in scheme 2 and relates to the addition of appropriately compounds of formula IX on aldehydes or ketones of formula VIII using a suitable base with subsequent reaction of the resulting alcohol function of formula V with a compound of formula VI to give a compound of formula Ib, where X1 has the abovementioned meanings.

Scheme 2

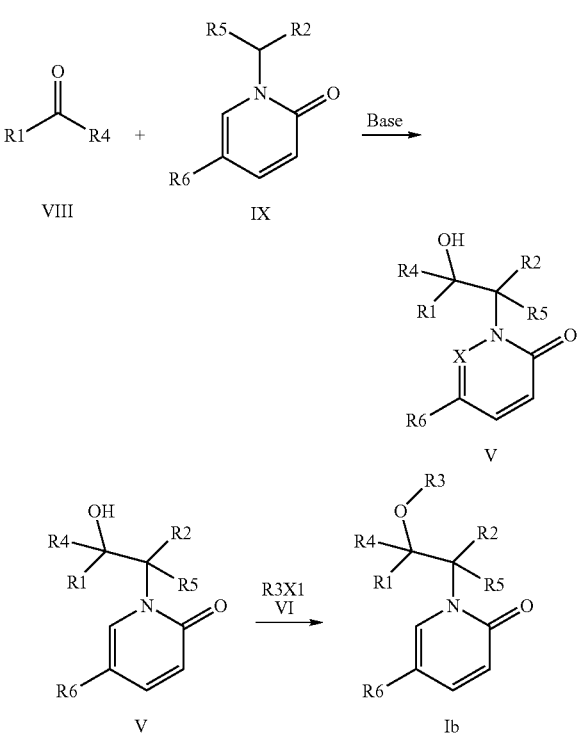

A further method for preparing the compounds of formula I is depicted in scheme 3 below. This method uses the ring opening of R1 and R2 substituted epoxides of formula XI by suitable compounds of formula XII with base catalysis as key step and affords, in contrast to the other methods, the products in diastereoisomerically pure form. The resulting alcohol of formula Vb is subsequently reacted with a compound of formula VI to give the compound of formula Ic, where X1 has the abovementioned meanings.

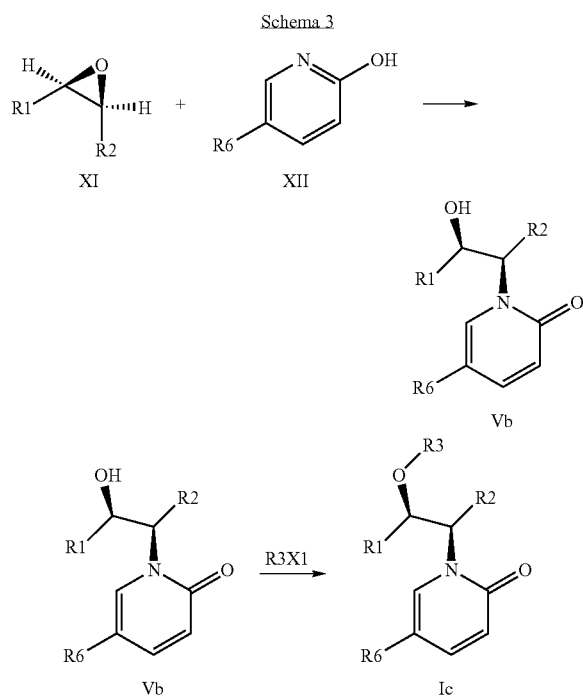

Schema 3

The starting compounds described in the synthetic methods, such as the compounds of formula II, III, VI, VIa, VII, IX, XI and XII can be purchased or can be prepared by or analogous to processes described in the literature and known to the skilled worker.

The working up and, if desired, the purification of the products and/or intermediates takes place by conventional methods such as extraction, chromatography or crystallization and conventional dryings.

The use of the compounds of formula I and their pharmaceutically acceptable salts as medicament is claimed.

The compounds of the invention of formula I and their pharmaceutically acceptable salts can thus be used on animals, preferably on mammals, and in particular on humans, as pharmaceuticals on their own, in mixtures with one another or in the form of pharmaceutical preparations.

The present invention also relates to the compounds of formula I and their pharmaceutically acceptable salts for use in the therapy and prophylaxis of the abovementioned diseases and to their use for producing medicaments for the abovementioned diseases and medicaments with a $K^+$ channel-blocking action.

Also claimed is a pharmaceutical preparation comprising an effective amount of a compound of formula I and/or of its pharmaceutically acceptable salts, together with pharmaceutically acceptable carriers and additives, alone or in combination with other pharmacological active ingredients or pharmaceuticals. The pharmaceutical preparations normally comprise from 0.1 to 90 percent by weight of the compounds of formula I and/or their pharmaceutically acceptable salts. The pharmaceutical preparations can be produced in a manner known per se. For this purpose, the compounds of formula I and/or their pharmaceutically acceptable salts are converted together with one or more solid or liquid pharmaceutical vehicles and/or excipients and, if desired, in combination with other pharmaceutical active ingredients into a suitable dosage form, which can then be used as pharmaceutical in human medicine or veterinary medicine.

Pharmaceuticals which comprise a compound of formula I and/or its pharmaceutically acceptable salts can moreover be administered for example orally, parenterally, intravenously, rectally, percutaneously, topically or by inhalation, and the preferred administration depends on the individual case, for example on the particular manifestation of the disorder. The compounds of formula I can moreover be used alone or together with pharmaceutical excipients, in particular both in veterinary and in human medicine. The pharmaceuticals comprise active ingredients of formula I and/or their pharmaceutically acceptable salts generally in an amount of from 0.01 mg to 1 g per dose unit.

The skilled worker is familiar on the basis of his expert knowledge with which excipients are suitable for the desired pharmaceutical formulation. Besides solvents, gel formers, suppository bases, tablet excipients and other active substance carriers it is possible to use for example antioxidants, dispersants, emulsifiers, antifoams, masking flavors, preservatives, solubilizers, agents for achieving a depot effect, buffer substances or colorants.

For a form for oral use, the active compounds are mixed with the additives suitable for this purpose, such as carriers, stabilizers or inert diluents, and converted by conventional methods into suitable presentations such as tablets, coated tablets, two-piece capsules, aqueous, alcoholic or oily solutions. Examples of inert carriers which can be used are gum arabic, magnesia, magnesium carbonate, potassium phosphate, lactose, glucose or starch, especially corn starch. Preparation can take place both as dry and as wet granules. Suitable as oily carriers or as solvents are, for example, vegetable or animal oils such as sunflower oil or fish liver oil. Suitable solvents for aqueous or alcoholic solutions are, for example, water, ethanol or sugar solutions or mixtures thereof. Examples of further excipients, also for other administration forms, are polyethylene glycols and polypropylene glycols.

For subcutaneous, intramuscular or intravenous administration, the active compounds are converted if desired with the substances usual for this purpose, such as solubilizers, emulsifiers or further excipients, into a solution, suspension or emulsion. The compounds of formula I and/or their pharmaceutically acceptable salts may also be lyophilized and the resulting lyophilizates be used, for example, for producing products for injection or infusion. Examples of suitable solvents are: water, physiological saline or alcohols, for example ethanol, propanol, glycerol, as well as sugar solutions such as glucose or mannitol solutions, or else mixtures of the various solvents mentioned.

Suitable as pharmaceutical formulations for administration in the form of aerosols or sprays are, for example, solutions, suspensions or emulsions of the active ingredient of formula I or their pharmaceutically acceptable salts in a pharmaceutically acceptable solvent, such as in particular ethanol or water, or a mixture of such solvents. The formulation may if required also comprise other pharmaceutical excipients such as surfactants, emulsifiers and stabilizers, and a propellant gas. Such a preparation comprises the active ingredient normally in a concentration of about 0.1 to 10, in particular of about 0.3 to 3 percent by weight.

The dosage of the active ingredient to be administered or of the pharmaceutically acceptable salts thereof depends on the individual case and should be adapted to the circumstances of the individual case as usual for an optimal effect. Thus, it naturally depends on the frequency of administration and on the potency and duration of action of the particular compounds employed for therapy or prophylaxis, but also on the type and severity of the disease to be treated, and on the gender, age, weight and individual response of the human or animal to be treated, and on whether therapy is acute or prophylactic.

The daily dose of a compound of formula I and/or its pharmaceutically acceptable salts for a patient weighing about 75 kg is normally at least 0.001 mg/kg to 100 mg/kg of body weight, preferably 0.01 mg/kg to 20 mg/kg. Even higher dosages may also be necessary for acute episodes of the disease, for example in an intensive care unit. Up to 800 mg per day may be necessary, especially on i.v. use, for instance for an infarct patient in an intensive care unit. The dose may be in the form of a single dose or be divided into a plurality, for example two, three or four, single doses. Parenteral administration by injection or infusion, for example a continuous intravenous infusion, may also be advantageous, especially in the treatment of acute cases of cardiac arrhythmias, for example in an intensive care unit.

The compounds of formula I and/or their pharmaceutically acceptable salts can also be combined with other pharmaceutical active ingredients to achieve an advantageous therapeutic effect. Thus, advantageous combinations with substances acting on the cardiovascular system are possible in the treatment of cardiovascular disorders. Suitable examples of such combination partners advantageous for cardiovascular disorders are other antiarrhythmics, i.e. class I, class II or class III antiarrhythmics, such as, for example, $IK_r$ channel blockers, for example dofetilide, or additionally substances which reduce blood pressure, such as ACE inhibitors (for example enalapril, captopril, ramipril), angiotensin antagonists, $K^+$ channel activators, and alpha- and beta-receptor blockers, but also sympathomimetic and adrenergic compounds, and $Na^+/H^+$ exchange inhibitors, calcium channel antagonists, phosphodiesterase inhibitors and other substances with a positive inotropic effect, such as, for example, digitalis glycosides, or diuretics. In particular, combinations with beta blockers or $IK_r$ channel blockers are of particular interest.

| List of abbreviations: | |
|---|---|
| tert-BuLi | Tertiary butyllithium |
| DMF | Dimethylformamide |
| DMSO | Dimethyl sulfoxide |
| TMEDA | N,N,N',N'-Tetramethylethylenediamine |

The compounds of formula I can be prepared by various processes. The preparation methods used to prepare the examples are described below, where R1, R2, R3, R4, R5, R6 and X have the same meaning as in compounds of formula I.

Method A:

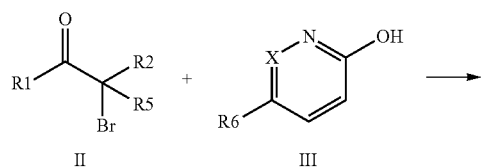

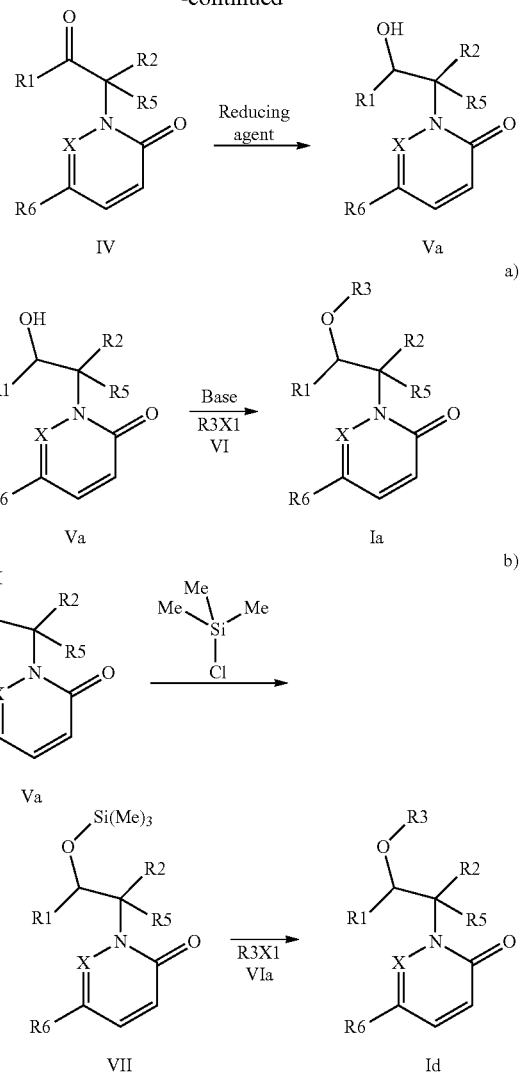

1 equivalent of a bromoketone of formula II was intimately mixed in a mortar with 1.5 to 2 equivalents of an R6-substituted 2-hydroxypyridine or 3-hydroxypyridazine of formula II, and the mixture was subsequently brought to a temperature of 100-120° C. After 2-6 hours, the mixture was dissolved in an organic solvent such as ethyl acetate or $CH_2Cl_2$ and purified by chromatographic methods. The resulting compound of formula IV was reduced, normally with excess $NaBH_4$ in methanol, to compounds of formula Va, resulting in two diastereomers. It was usually possible at this stage to separate the isomers easily by conventional chromatographic methods, for example by separation on silica gel using heptane/ethyl acetate mixtures as eluant, whereas this was often possible only with difficulty at later stages.

The intermediates of formula Va obtained in this way could be alkylated to the compounds of formula Ia as follows:

a) The compounds of formula Va were dissolved in a dipolar aprotic solvent such as, for example, DMSO or DMF, and 1-20 mole equivalents of a base such as, for example, powdered NaOH or NaH were added. 3-5 mole equivalents of a compound of formula VI such as, for example, cyclopropylmethyl bromide or 4-CN-fluorobenzene, where X1 is defined for example as halogen such as fluorine, chlorine, bromine or iodine, in particular fluorine or bromine, were added at room temperature. The mixture was stirred at room temperature for 1-10 hours until conversion was complete, and further equivalents of the compound of formula VI were added where appropriate (variant Aa). For workup, the reaction mixture was usually diluted with water and, in the event that the products do not separate out as crystals, extracted with ethyl acetate and purified where appropriate by chromatography.

b) In the case where the compound of formula VI is an arylating agent, it was possibly advantageous to subject the compound of formula Va firstly to a silylation, for example by reaction with 1.1 equivalents of each of trimethylsilyl chloride and pyridine in methylene chloride, and then to react the arylating agent of formula VIa, where X1 is defined for example as halogen such as fluorine, chlorine, bromine or iodine, in the presence of a reagent which eliminates silyl groups, such as, for example, tetrabutylammonium fluoride, in a suitable solvent such as DMF, at temperatures of 20-120° C. This process is particularly advantageous for base-labile compounds of formula Id (variant Ab). Workup of the products took place in analogy to variant Aa.

Method B:

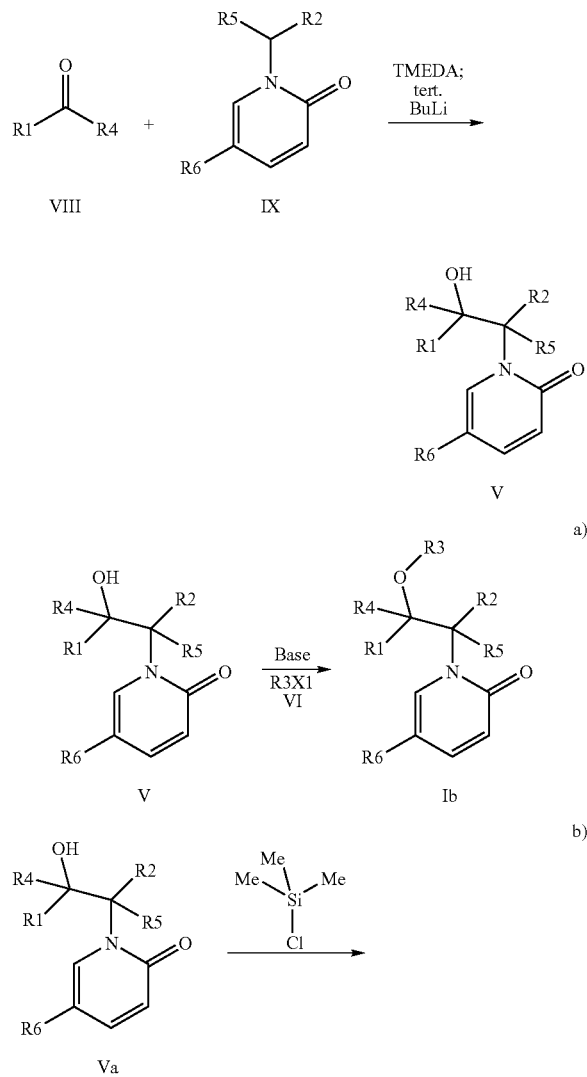

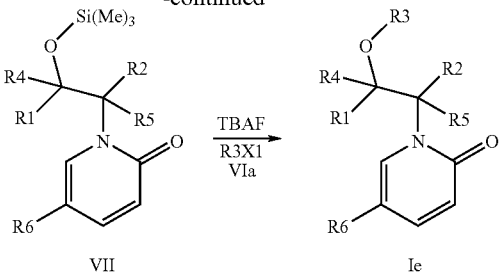

7.5 equivalents of a compound of formula VIII plus 5 equivalents of a compound of formula IX and 5.5 equivalents of N,N,N',N'-tetramethylethylenediamine were dissolved in 10 ml of absolute THF and cooled to −70° C., and 5.6 equivalents of tert-butyllithium were added. After the usual workup, for example by adding a saturated solution of ammonium chloride and extracting with ethyl acetate, the mixture of the diastereoisomeric compound of formula V could be purified by chromatographic methods and, in some cases, also be separated into its individual components. The intermediates of formula V obtained in this way were converted into the compounds of formula Ib as follows:

a) 1 equivalent of a compound of formula V was dissolved in a dipolar aprotic solvent such as, for example, DMSO or DMF, and 1-20 mole equivalents of a base such as, for example, powdered NaOH or NaH were added. 3-5 mole equivalents of a compound of formula VI such as, for example, cyclopropylmethyl bromide or 4-CN-fluorobenzene, where X1 is defined for example as halogen such as fluorine, chlorine, bromine or iodine, in particular fluorine or bromine, were added at room temperature. The mixture was stirred at room temperature for 1-10 hours until conversion was complete, and further equivalents of the compound of formula VI were added where appropriate (variant Ba). For workup, the reaction mixture was usually diluted with water and, in the event that the products do not separate out as crystals, extracted with ethyl acetate and purified where appropriate by chromatography.

b) In the case where the compound of formula VI is an arylating agent, it was possibly advantageous to subject the compound of formula Va firstly to a silylation, for example by reaction with 1.1 equivalents of each of trimethylsilyl chloride and pyridine in methylene chloride, and then to react the arylating agent of formula VIa, where X1 is defined for example as halogen such as fluorine, chlorine, bromine or iodine, in particular fluorine or bromine, in the presence of a reagent which eliminates silyl groups, such as, for example, tetrabutylammonium fluoride, in a suitable solvent such as DMF, at temperatures of 20-120° C. This process is particularly advantageous for base-labile compounds of formula Ie (variant Bb). Workup of the products took place in analogy to variant Ba.

Variant C:

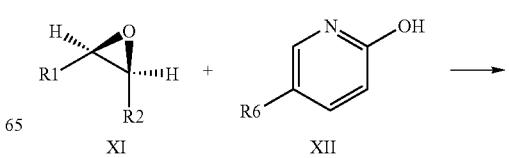

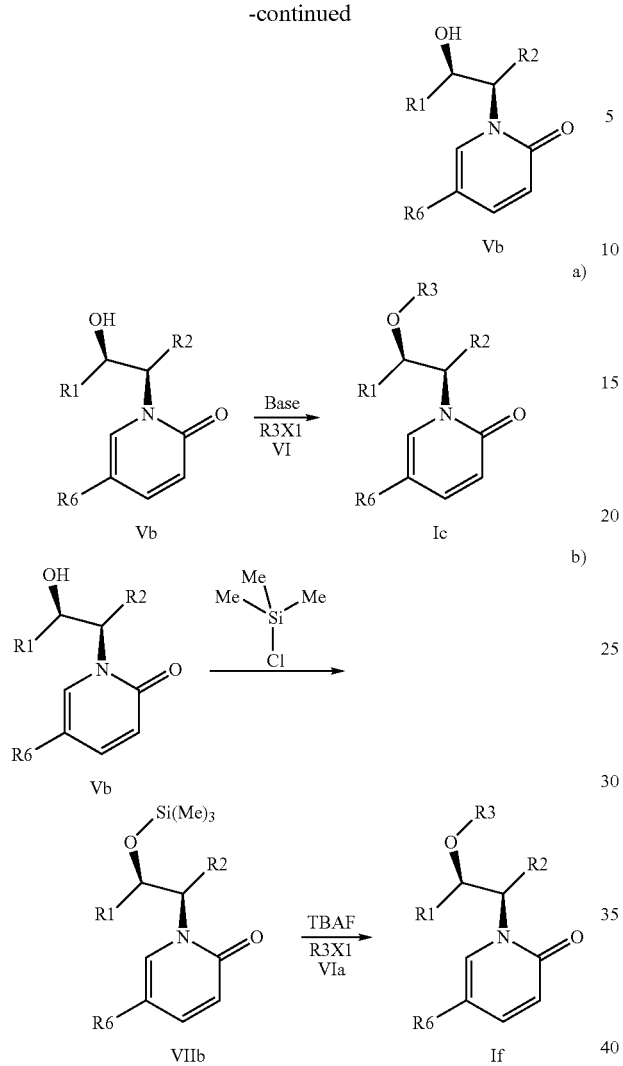

1 equivalent of an R1- and R2-substituted cis-stilbene oxide of formula XI was dissolved in dimethylformamide and stirred with a 20-50% excess of a compound of formula XII and with a strong base such as, for example, sodium hydride at 80-100° C. for several hours. The resulting alcohols of formula Vb were usually sterically uniform and, as a consequence of the known geometry of the epoxide ring opening under basic conditions, exhibited a trans arrangement of the oxygen and nitrogen substituents.

The intermediates of formula Vb obtained in this way were converted into the compounds of formula Ic as follows:

a) 1 equivalent of a compound of formula Vb was dissolved in a dipolar aprotic solvent such as, for example, DMSO or DMF, and 1-20 mole equivalents of a base such as, for example, powdered NaOH or NaH were added. 3-5 mole equivalents of a compound of formula VI such as, for example, cyclopropylmethyl bromide or 4-CN-fluorobenzene, where X1 is defined for example as halogen such as fluorine, chlorine, bromine or iodine, in particular fluorine or bromine, were added at room temperature. The mixture was stirred at room temperature for 1-10 hours until conversion was complete, and further equivalents of the compound of formula VI were added where appropriate (variant Ca). For workup, the reaction mixture was usually diluted with water and, in the event that the products do not separate out as crystals, extracted with ethyl acetate and purified where appropriate by chromatography.

b) In the case where the compound of formula VI is an arylating agent, it was possibly advantageous to subject the compound of formula Va firstly to a silylation, for example by reaction with 1.1 equivalents of each of trimethylsilyl chloride and pyridine in methylene chloride, and then to react the arylating agent of formula VIa, where X1 is defined for example as halogen such as fluorine, chlorine, bromine or iodine, in particular fluorine or bromine, in the presence of a reagent which eliminates silyl groups, such as, for example, tetrabutylammonium fluoride, in a suitable solvent such as DMF, at temperatures of 20-120° C. This process is particularly advantageous for base-labile compounds of formula If (variant Cb). Workup of the products took place in analogy to variant Ca.

The starting compounds described in the synthetic methods, such as the compounds of formula II, III, VI, VIa, VII, IX, XI and XII can be purchased or can be prepared by or analogous to processes described in the literature and known to the skilled worker.

The working up and, if desired, the purification of the products and/or intermediates takes place by conventional methods such as extraction, chromatography or crystallization and conventional dryings.

Examples for the use of the general synthetic methods:

Example 1

1R',2R'-1-(2-Cyclopropylmethoxy-1,2-diphenylethyl)-1H-pyridin-2-one

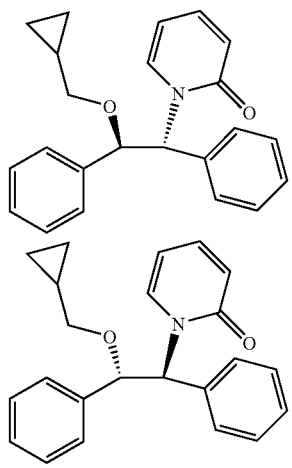

a) Racemic cis-stilbene oxide (100 mg, 0.51 mmol) was dissolved in absolute DMF, and 18.36 mg of a suspension of sodium hydride (90% in oil) and 72.75 mg of 2-hydroxypyridine were added, and the mixture was stirred at 80° C. under argon for 4 hours. The mixture was worked up with water/ethyl acetate and chromatographed on silica gel with ethyl acetate/n-heptane 1:1. 1-(2-Hydroxy-1,2-diphenylethyl)-1H-pyridin-2-one was obtained first, 42 mg, 28% as sterically uniform compound which, on the basis of the known steric course of epoxide ring openings under basic conditions, was assigned the trans arrangement of the hydroxy group and the pyridine ring, corresponding to a relative 1R',2R' configuration of centers 1 and 2:

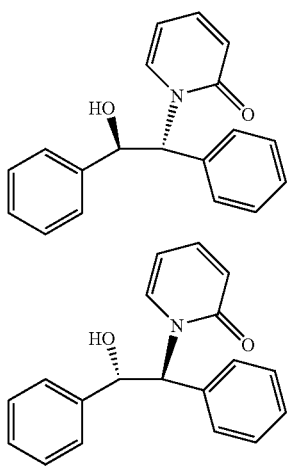

b) 50 mg (0.171 mmol) of the compound obtained in stage a) were dissolved in 1 ml of DMSO, and 51 mg of powdered NaOH and 58.44 mg of cyclopropylmethyl bromide (0.433 mmol) were added. After stirring at room temperature for 2 hours, the mixture was diluted with water, and the precipitated crystals were filtered off with suction and, after drying in air, stirred with n-heptane. 30 mg (51%) of the desired product 1R',2R'-1-(2-cyclopropylmethoxy-1,2-diphenylethyl)-1H-pyridin-2-one were obtained.

Example 2

1R',2S'-1-[2-Cyclopropylmethoxy-1-(4-fluorophenyl)-2-(4-methoxy-phenyl)ethyl]-1H-pyridin-2-one

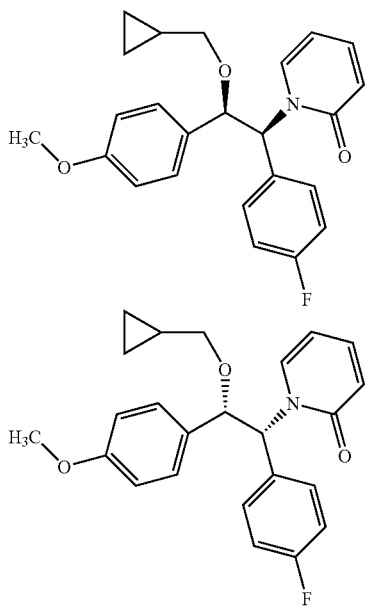

a) 1.015 g (5 mmol) of 1-(4-fluorobenzyl)-1H-pyridin-2-one plus 1.016 g of p-methoxybenzaldehyde and 0.638 g (5.5 mmol) of N,N,N',N'-tetramethylethylenediamine were dissolved in 10 ml of tetrahydrofuran and cooled in an acetone/dry ice bath to −60° C. A solution of tert-butyllithium, 1.7 molar in n-heptane (3.8 ml, 5.5 mmol) was added dropwise over the course of 30 minutes. The mixture was allowed to reach room temperature over the course of one hour and was acidified with a saturated ammonium chloride solution. After the usual workup, the reaction mixture was chromatographed on silica gel (50 g) with n-heptane/ethyl acetate. 294 mg of the faster-migrating diastereoisomeric cis alcohol were obtained:

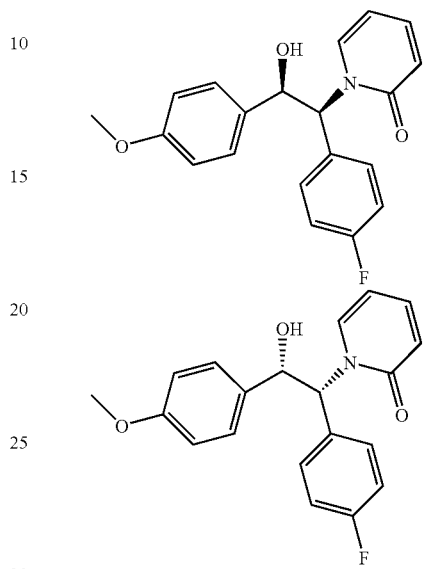

and 352 mg of a 1:1 mixture of the cis/trans alcohols.

b) 198 mg of the cis alcohol obtained in stage a) were subsequently dissolved in 2 ml of DMSO and stirred with 200 mg of powdered NaOH and 200 mg of bromomethyl-cyclopropane at room temperature for 20 minutes. The usual aqueous workup and chromatography on silica gel with n-heptane/ethyl acetate 2:1 resulted in 51 mg of the desired final product 1R',2S'-1-[2-cyclopropylmethoxy-1-(4-fluorophenyl)-2-(4-methoxy-phenyl)ethyl]-1H-pyridin-2-one.

Example 3

1-(2-Cyclopropylmethoxy-1,2-diphenylethyl)-5-fluoro-1H-pyridin-2-one

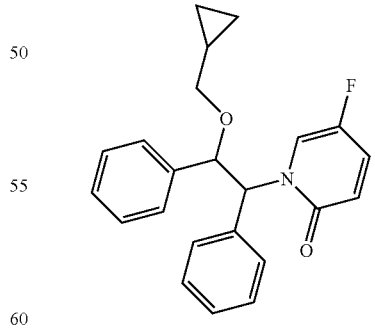

a) 1.2 g (4.36 mmol) of 2-bromo-1,2-diphenylethanone and 740 mg (6.54 mmol) of 5-fluoro-2-hydroxypyridine were intimately ground in a mortar, and the mixture was subsequently heated at 120° C. for 2 hours. The still hot, oily mass was dissolved in ethyl acetate. Cooling resulted in the 5-fluoro-1-(2-oxo-1,2-diphenylethyl)-1H-pyridin-2-one in crystalline form, 1.01 g (75%), which was immediately dissolved in 15 ml of methanol. After addition of 340 mg (9.03 mmol) of sodium borohydride, the mixture was left at room temperature for one hour and then diluted with water. The resulting mass of crystals was filtered off with suction. The product contains the diastereoisomeric pyrid-2-one alcohols in the ratio of about 1:2 and was not fractionated further.

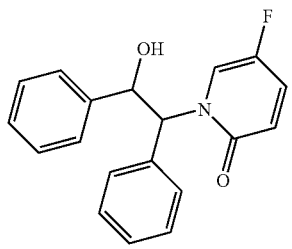

b) 250 mg of the mixture of diastereoisomeric alcohols obtained in stage a) were dissolved in 2.5 ml of DMSO and stirred with 242 mg of powdered NaOH and 273 mg of bromomethylcyclopropane at room temperature for 3 hours. The usual aqueous workup was followed by chromatography on silica gel with n-heptane/ethyl acetate 1:1. The desired final product 1-(2-cyclopropylmethoxy-1,2-diphenyl ethyl)-5-fluoro-1H-pyridin-2-one was obtained in a yield of 90 mg (31%).

Example 4

2-[2-(4-Chlorophenyl)-2-cyclopropylmethoxy-1-phenylethyl]-2H-pyridazin-3-one

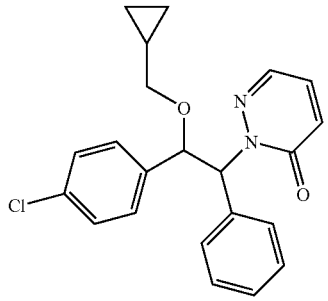

a) 1 g (3.22 mmol) of 2-bromo-1-(4-chlorophenyl)-2-phenylethanone were melted together with 0.7 g (7.28 mmol) of pyridazin-3-one at 120° C. for 3 h. The black residue was dissolved in hot CH$_2$Cl$_2$ and chromatographed on 50 g of silica gel. 80 mg of cream-colored crystals were obtained: 2-[2-(4-chlorophenyl)-2-oxo-1-phenylethyl]-2H-pyridazin-3-one.

b) The intermediate obtained in stage a) was dissolved in 0.5 ml of methanol and treated with sodium borohydride (50 mg) for 1 hour. The usual workup resulted in a mixture of the diastereoisomeric alcohols:

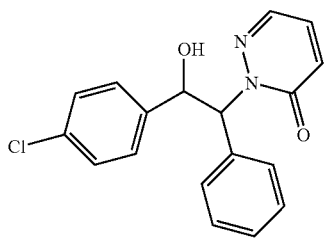

c) The intermediate obtained in stage b) was reacted with bromomethylcyclopropane under the conditions described in example 3 to give the desired final product. Chromatography on 10 g of silica gel were employed for purification, resulting in 16 mg of 2-[2-(4-chlorophenyl)-2-cyclopropylmethoxy-1-phenylethyl]-2H-pyridazin-3-one.

Example 5

1R',2R'-5-Fluoro-1-(2-p-cyanophenoxy-1,2-di-p-fluorophenylethyl)-1H-pyridin-2-one

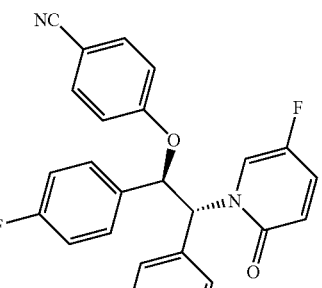

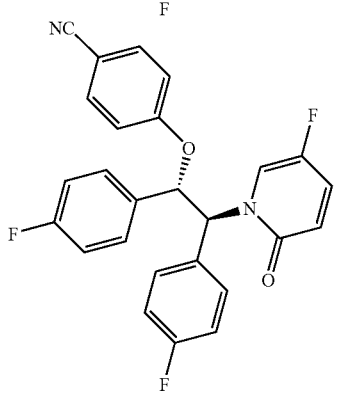

a) 345 mg (1 mmol) of a diastereoisomeric mixture of 6-fluoro-1-(2-hydroxy-1,2-di-p-fluorophenylethyl)-1H-pyridin-2-one obtained by general method A from 2-bromo-1,2-bis(4-fluorophenyl)ethanone and 5-fluoro-2-hydroxypyridine was dissolved in 3.5 ml of methylene chloride, and 79 mg of pyridine (1 mmol) and 120 mg (1.1 mmol) of trimethylsilyl chloride were added. After the mixture had stood at room temperature for 5 hours it was put, without workup and under argon, onto a 50 g silica gel column and chromatographed with the eluant heptane/ethyl acetate. 150 mg of a faster-migrating diastereoisomeric mixture of the silyl alcohols, and 220 mg of the pure diastereoisomeric silyl alcohol with the following stereochemistry, i.e. a relative configuration of 1R',2R' at centers 1 and 2, were obtained:

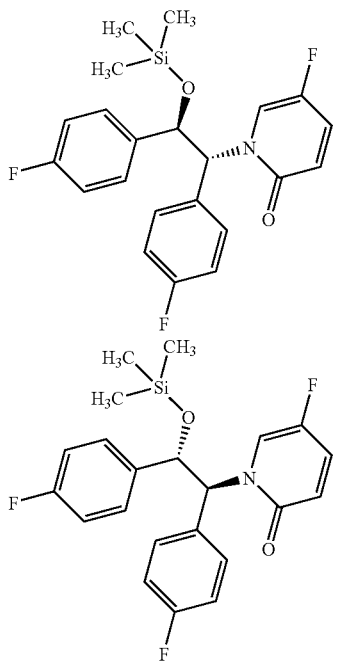

b) 170 mg (0.41 mmol) of the silylated alcohol obtained in stage a) were left with 170 mg (1.4 mmol) of p-CN-fluorobenzene and 220 mg (0.84 mmol) of tetrabutyl-ammonium fluoride in 2.5 ml of absolute DMF at room temperature overnight. After workup with ethyl acetate and water, the residue was chromatographed on silica gel. Heptane/ethyl acetate 2:1 eluted 100 mg (55%) of the desired final product 1R',2R'-5-fluoro-1-(2-p-cyanophenoxy-1,2-di-p-fluorophenylethyl)-1H-pyridin-2-one.

Example 6

1-[2-Cyclopropoxy-1,2-bis-(4-fluorophenyl)ethyl]-5-fluoro-1H-pyridin-2-one

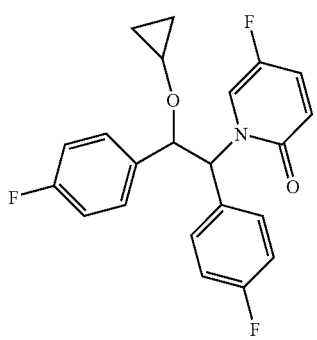

a) 102 mg (0.3 mmol) of a diastereoisomeric mixture of 6-fluoro-1-(2-hydroxy-1,2-di-p-fluorophenylethyl)-1H-pyridin-2-one obtained by general method A from 2-bromo-1,2-bis-(4-fluorophenyl)ethanone and 5-fluoro-2-hydroxypyridine were dissolved in 1.5 ml of THF, and 0.5 ml of butyl vinyl ether was added. The following are added in the stated sequence: 20 mg of 3,7-diphenyl-o-phenanthroline (0.06 mmol), 20 mg of palladium bistrifluoroacetate (0.06 mmol) and 36 mg of triethylamine (0.35 mmol). The mixture was stirred while heating at 80° C. under argon for 2 hours. It was then worked up with water and ethyl acetate and, after evaporation of the solvent, the residue was chromatographed on 20 g of silica gel with n-heptane-ethyl acetate in the ratio 2:1. 41 mg of 1-[2-vinyloxy-1,2-bis-(4-fluorophenyl)ethyl]-5-fluoro-1-pyridin-2-one were obtained.

b) 42 mg of the intermediate obtained in stage a) were dissolved in 2 ml absolute methylene chloride, and 0.54 ml of a solution of diethyl zinc (1.1 molar in toluene) and then 0.1 ml of methylene iodide were added, and the mixture was stirred at room temperature for 3 hours. The mixture was diluted with water and extracted twice with ethyl acetate. The ethyl acetate phases were washed with water until neutral, dried with magnesium sulfate and concentrated. The residue was chromatographed on 20 g of silica gel with the eluant heptane/ethyl acetate 2:1. The desired final product 1-[2-cyclopropoxy-1,2-bis-(4-fluorophenyl)ethyl]-5-fluoro-1H-pyridin-2-one is obtained in a yield of 35 mg.

The following examples were prepared in analogy to the synthetic methods described above:

| Example No. | Structure | Synthesis by general method: |
|---|---|---|
| 1 | 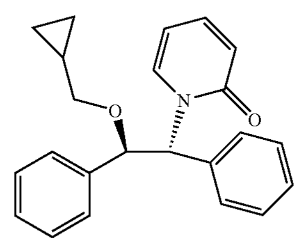 | Ca |
| | | Ba |
| 2 | 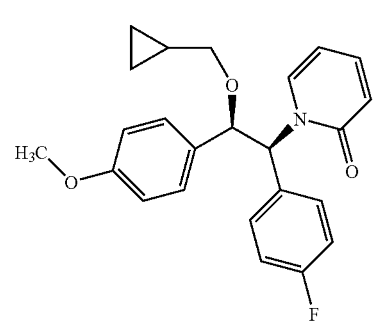 | Ba |

25
-continued
| Example No. | Structure | Synthesis by general method: |
|---|---|---|
|  | 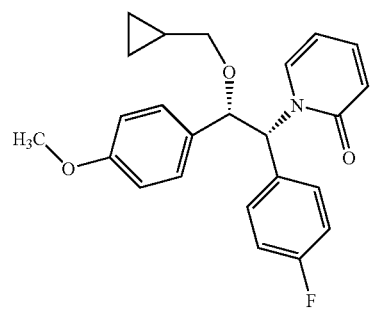 |  |
| 3 | 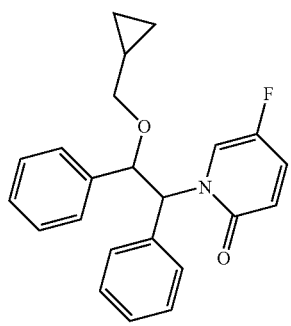 | Aa |
| 4 | 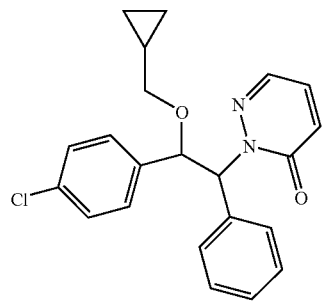 | Aa |
| 5 | 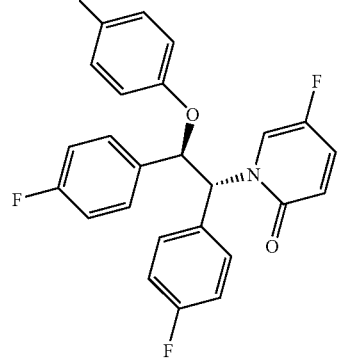 | Ab |
26
-continued
| Example No. | Structure | Synthesis by general method: |
|---|---|---|
|  | 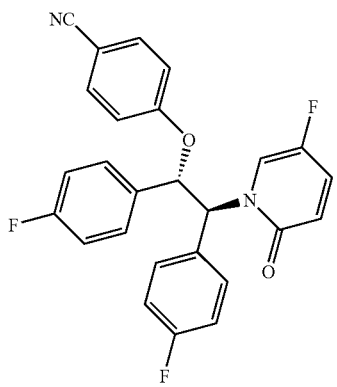 |  |
| 6 | 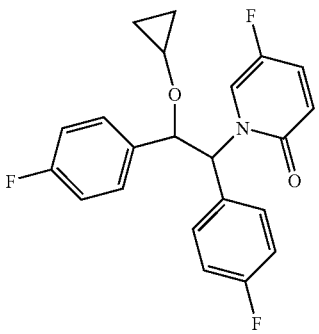 | A |
| 7 | 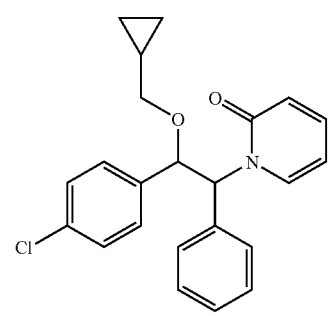 | Aa |
| 8 | 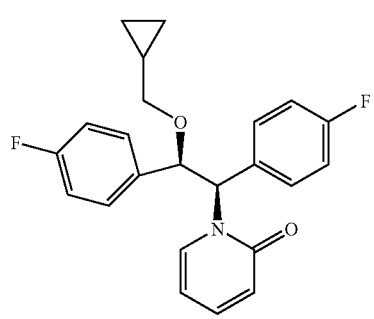 | Ba |

| Example No. | Structure | Synthesis by general method: |
|---|---|---|
| | 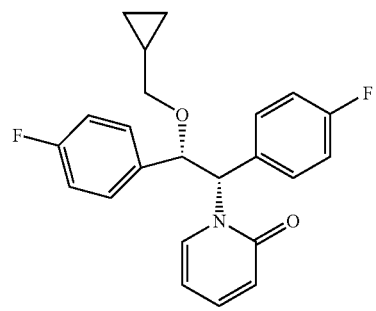 | |
| 9 | 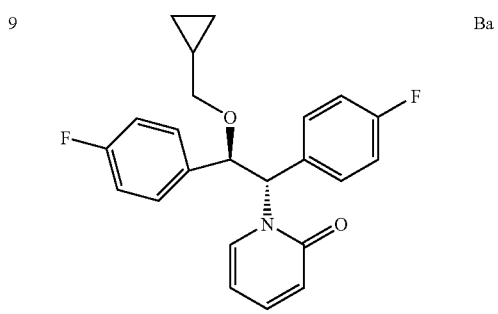 | Ba |
| | 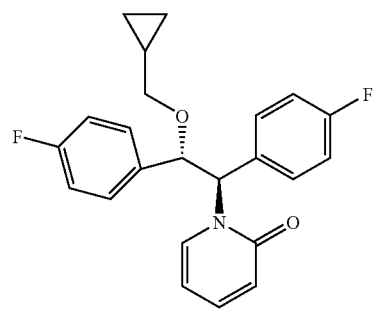 | |
| 10 | 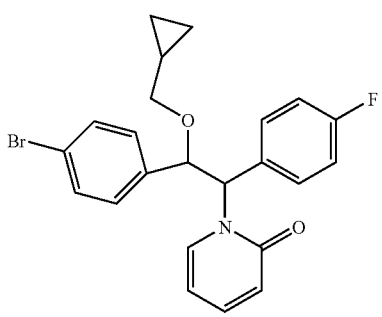 | Ba |
| 11 | 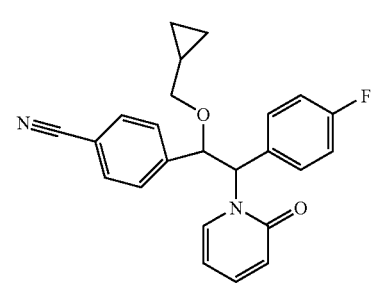 | Ba |
| Example No. | Structure | Synthesis by general method: |
|---|---|---|
| 12 | 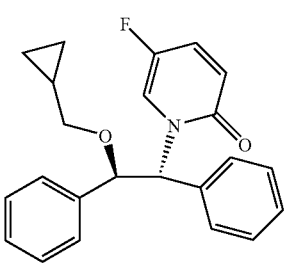 | Ca |
| | 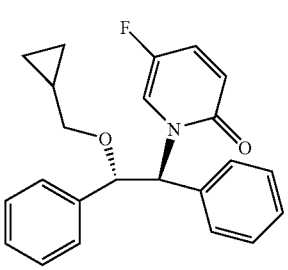 | |
| 13 | 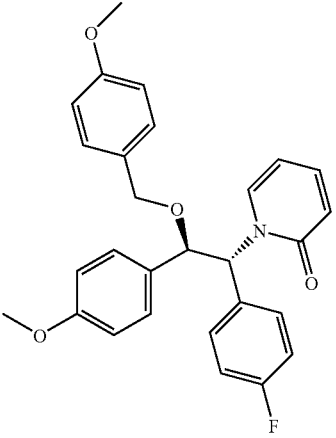 | Aa |
| | 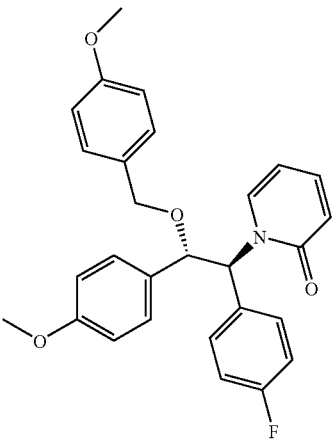 | |

| Example No. | Structure | Synthesis by general method: |
|---|---|---|
| 14 | 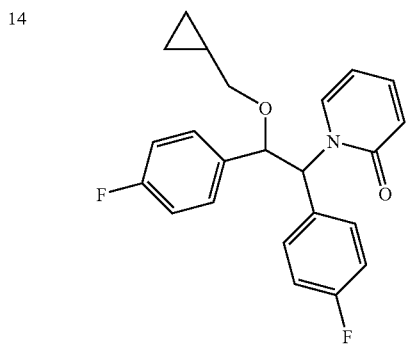 | Aa |
| 15 | 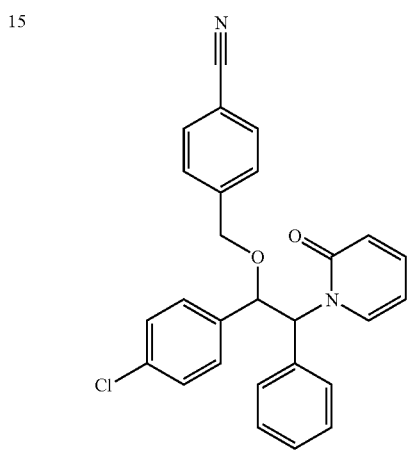 | Aa |
| 16 | 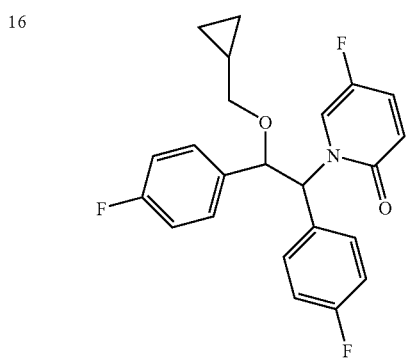 | Ba |
| 17 | 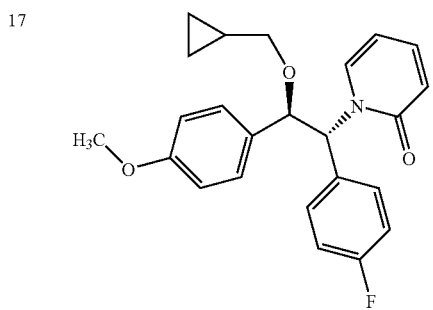 | Ba |

| Example No. | Structure | Synthesis by general method: |
|---|---|---|
| | 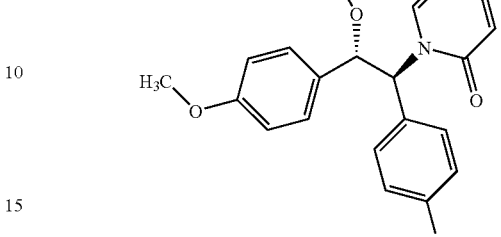 | |
| 18 | 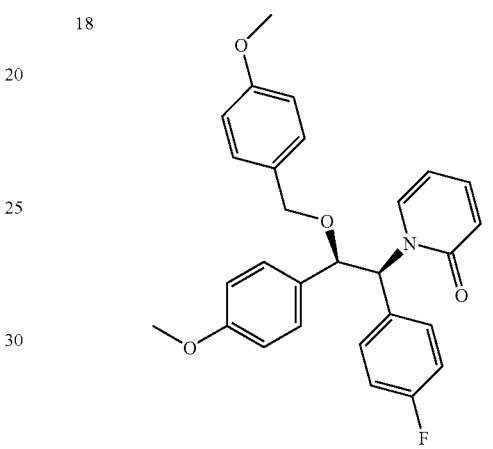 | Aa |
| | 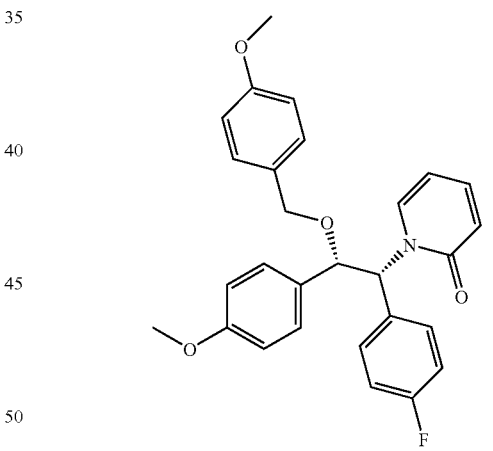 | |

Compounds with stated absolute stereochemistry were obtained as pure enantiomers of the depicted structure. Compounds stated to be in the form of two enantiomers were obtained as racemic mixture of the two depicted enantiomers. Structures where the stereochemistry is not stated represent racemic mixtures of the possible diastereomers.

Pharmacological Investigations

Determination of the Activity on the Kv1.5 Channel

Human Kv1.5 channels were expressed in xenopus oocytes. For this purpose, firstly oocytes were isolated from *Xenopus laevis* and defolliculated. Kv1.5-encoding RNA synthesized in vitro was then injected into these oocytes. After Kv1.5 protein expression for 1-7 days, Kv1.5 currents were measured on the oocytes using the two-microelectrode voltage clamp technique. The Kv1.5 channels were in this case usually activated with voltage jumps lasting 500 ms to 0 mV and 40 mV. A solution of the following composition flowed through the bath: NaCl 96 mM, KCl 2 mM, CaCl$_2$ 1.8 mM, MgCl$_2$ 1 mM, HEPES 5 mM (titrated to pH 7.4 with NaOH). These experiments were carried out at room temperature. The following were employed for data acquisition and analysis: Geneclamp amplifier (Axon Instruments, Foster City, USA) and MacLab D/A converter and software (AD-instruments, Castle Hill, Australia). The substances of the invention were tested by adding them in various concentrations to the bath solution. The effects of the substances were calculated as percent inhibition of the Kv1.5 control current which was obtained when no substance was added to the solution. The data were then extrapolated using the Hill equation in order to determine the inhibitory concentrations IC$_{50}$ for the respective substances.

Determination of the Activity on the TASK-1 Channel

Human TASK-1 channels were expressed in xenopus oocytes. For this purpose, firstly oocytes were isolated from *Xenopus laevis* and defolliculated. TASK-1-encoding RNA synthesized in vitro was then injected into these oocytes. After TASK-1 protein expression for 2 days, TASK-1 currents were measured on the oocytes using the two-microelectrode voltage clamp technique. The TASK-1 channels were in this case usually activated with voltage jumps lasting 250 ms to 40 mV. A solution of the following composition flowed through the bath: NaCl 96 mM, KCl 2 mM, CaCl$_2$ 1.8 mM, MgCl$_2$ 1 mM, HEPES 5 mM (titrated to pH 7.4 with NaOH). These experiments were carried out at room temperature. The following were employed for data acquisition and analysis: Geneclamp amplifier (Axon Instruments, Foster City, USA) and MacLab D/A converter and software (ADinstruments, Castle Hill, Australia). The substances of the invention were tested by adding them in various concentrations to the bath solution. The effects of the substances were calculated as percent inhibition of the TASK-1 control current which was obtained when no substance was added to the solution. The data were then extrapolated using the Hill equation in order to determine the half-maximum inhibitory concentrations (IC$_{50}$) for the respective substances.

Determination of the Activity on the KACh Channel

The effect of the substances on the acetylcholine-activated potassium channel was investigated using the micropunction technique on isolated guinea pig atria. Following sacrifice by cervical dislocation and severance of the spinal column, the heart was removed, and the left atrium was detached with fine scissors and fastened in a measuring chamber. A modified Krebs-Henseleit solution (in mmol/l: 136 NaCl, 1.0 KCl, 1.2 KH$_2$PO$_4$, 1.1 MgSO$_4$, 1.0 CaCl$_2$, 5 glucose, 10 HEPES, pH=7.4) flowed continuously over the tissue. The temperature in the measuring chamber was 37° C. The atrium was stimulated with a square-wave pulse of 1 to 4 volts lasting 1 to 3 milliseconds with a frequency of 1 Hz. The action potential was recorded using a glass microelectrode which was filled with 3 mol/l of KCl. The electrical signal was picked up by an amplifier (model 309 microelectrode amplifier, Hugo Sachs, March-Hugstetten, Germany) and stored and analyzed in a computer. Experimental outline: after an equilibration time of 30 min, 1 μmol/l carbachol was added in order to activate the K$_{ACh}$ ion channels by stimulating muscarinic receptors. This led to a marked shortening of the action potential duration at 90% repolarization (APD$_{90}$) of about 150 ms (without carbachol) to 50 ms after addition of carbachol (Gertjegerdes W., Ravens U., Zeigler A. (1979) Time course of carbachol-induced responses in guinea pig atria under the influence of oubain, calcium, and rate of stimulation. J. Cardiovasc. Pharmacol. 1: 235-243). Carbachol was present in the bath solution in all further measurements. After 30 min, 3 μmol/l of the substance to be measured were added and, after a further 30 min, the action potential was recorded. Blocking of K$_{ACh}$ channels leads to a prolongation of the APD$_{90}$. After a further 30 min, the substance concentration was raised to 10 μmol/l, and the measurement was carried out after an exposure time of 30 min. The percentage prolongation of the shortening of the APD$_{90}$ brought about by carbachol was calculated as the effect of the substance, the shortening by carbachol being set equal to 100%. A curve fitting was carried out with the calculated measurements using the logistic function:

$$F(x)=y_o+ax^n/(c^n+x^n),$$

where $c$ is the IC$_{50}$ and $n$ is the Hill coefficient.

The following IC$_{50}$ values were determined for the following compounds of formula I:

| Example No. | Kv1.5 IC-50 [μM] | mTask-1 IC-50 [μM] | KACh IC-50 [μM] |
|---|---|---|---|
| 1 | 0.38 | | |
| 2 | 1.30 | | |
| 3 | 0.78 | | ~10 |
| 4 | 1.05 | | |
| 5 | approx. 20-50 | | |
| 6 | 6.48 | | |
| 7 | 0.18 | | |
| 8 | 0.33 | | |
| 9 | 0.41 | 3.1 | |
| 10 | 0.87 | | |
| 11 | 2.03 | | |
| 12 | 1.47 | | |
| 13 | 4.48 | | |
| 14 | 1.40 | | |
| 15 | 2.51 | | |
| 16 | 4.56 | | |
| 17 | 1.83 | | |
| 18 | 2.69 | | |

What is claimed is:

1. A compound of formula I,

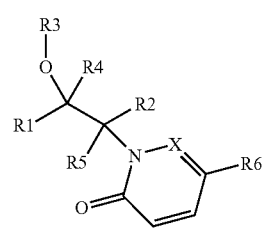

in which:
R1 is phenyl which is unsubstituted or substituted by 1, 2 or 3 substituents selected from the group consisting of F, Cl, Br, I, CN, alkoxy having 1, 2, 3 or 4 carbon atoms, OCF$_3$, methylsulfonyl, CF$_3$, alkyl having 1, 2, 3 or 4 carbon atoms, dimethylamino, sulfamoyl, acetyl, and methylsulfonylamino;

R2 is phenyl or naphthyl,
where each of these aryl radicals is unsubstituted or substituted by 1, 2 or 3 substituents selected from the group consisting of F, Cl, Br, I, CN, COOMe, CONH$_2$, alkoxy having 1, 2, 3 or 4 carbon atoms, OCF$_3$, OH, methylsulfonyl, CF$_3$, alkyl having 1, 2, 3 or 4 carbon atoms, dimethylamino, sulfamoyl, acetyl, and methylsulfonylamino;

R3 is $C_pH_{2p}$—R7;
   p is 0, 1, 2, 3, 4 or 5;
R7 is $CH_3$, $CH_2F$, $CHF_2$, $CF_3$, cycloalkyl having 3, 4, 5, 6 or 7 carbon atoms, C≡CH, C≡C—$CH_3$, alkoxy having 1, 2, 3 or 4 carbon atoms, or phenyl,
   where phenyl is unsubstituted or substituted by 1, 2 or 3 substituents selected from the group consisting of F, Cl, Br, I, $CF_3$, $OCF_3$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R4 is hydrogen or alkyl having 1, 2 or 3 carbon atoms;
R5 is hydrogen or alkyl having 1, 2 or 3 carbon atoms;
R6 is hydrogen, F, Cl, $CF_3$ or alkyl having 1, 2 or 3 carbon atoms;
X is CH;
or a pharmaceutically acceptable salt or trifluoroacetate thereof.

2. A compound of formula I as claimed in claim 1, in which:
R1 is phenyl which is unsubstituted or substituted by 1, 2 or 3 substituents selected from the group consisting of F, Cl, Br, I, CN, alkoxy having 1, 2, 3 or 4 carbon atoms, $OCF_3$, methylsulfonyl, $CF_3$, alkyl having 1, 2, 3 or 4 carbon atoms, dimethylamino, sulfamoyl, acetyl, and methylsulfonylamino;
R2 is phenyl, 1-naphthyl, or 2-naphthyl,
   where each of these aryl radicals is unsubstituted or substituted by 1, 2 or 3 substituents selected from the group consisting of F, Cl, Br, I, CN, COOMe, $CONH_2$, alkoxy having 1, 2, 3 or 4 carbon atoms, $OCF_3$, OH, methylsulfonyl, $CF_3$, alkyl having 1, 2, 3 or 4 carbon atoms, dimethylamino, sulfamoyl, acetyl, and methylsulfonylamino;
R3 is $C_pH_{2p}$-R7;
   p is 0, 1, 2, 3, 4 or 5;
R7 is $CH_3$, $CH_2F$, $CHF_2$, $CF_3$, cycloalkyl having 3, 4, 5, 6 or 7 carbon atoms, C≡CH, C≡C—$CH_3$, alkoxy having 1, 2, 3 or 4 carbon atoms, or phenyl,
   where phenyl is unsubstituted or substituted by 1, 2 or 3 substituents selected from the group consisting of F, Cl, Br, I, $CF_3$, $OCF_3$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R4 is hydrogen or alkyl having 1, 2 or 3 carbon atoms;
R5 is hydrogen or alkyl having 1, 2 or 3 carbon atoms;
R6 is hydrogen, F, Cl, $CF_3$ or alkyl having 1, 2 or 3 carbon atoms;
X is CH;
or a pharmaceutically acceptable salt or trifluoroacetate thereof.

3. A compound of formula I as claimed in claim 1, in which:
R1 is phenyl,
   which is unsubstituted or substituted by 1, 2 or 3 substituents selected from the group consisting of F, Cl, Br, I, CN, alkoxy having 1, 2, 3 or 4 carbon atoms, $OCF_3$, methylsulfonyl, $CF_3$, alkyl having 1, 2, 3 or 4 carbon atoms, dimethylamino, sulfamoyl, acetyl, and methylsulfonylamino;
R2 is phenyl,
   which is unsubstituted or substituted by 1, 2 or 3 substituents selected from the group consisting of F, Cl, Br, I, CN, COOMe, $CONH_2$, alkoxy having 1, 2, 3 or 4 carbon atoms, $OCF_3$, OH, methylsulfonyl, $CF_3$, alkyl having 1, 2, 3 or 4 carbon atoms, dimethylamino, sulfamoyl, acetyl, and methylsulfonylamino;
R3 is $C_pH_{2p}$-R7;
   p is 0, 1, 2, 3, 4 or 5;
R7 is $CH_3$, $CH_2F$, $CHF_2$, $CF_3$, cycloalkyl having 3, 4, 5, 6 or 7 carbon atoms, C≡CH, C≡C—$CH_3$, alkoxy having 1, 2, 3 or 4 carbon atoms, or phenyl,
   where phenyl is unsubstituted or substituted by 1, 2 or 3 substituents selected from the group consisting of F, Cl, Br, I, $CF_3$, $OCF_3$, CN, COOMe, $CONH_2$, COMe, OH, alkyl having 1, 2, 3 or 4 carbon atoms, alkoxy having 1, 2, 3 or 4 carbon atoms, dimethylamino, sulfamoyl, methylsulfonyl and methylsulfonylamino;
R4 is hydrogen;
R5 is hydrogen;
R6 is hydrogen, F or alkyl having 1, 2, or 3 carbon atoms;
X is CH;
or a pharmaceutically acceptable salt or trifluoroacetate thereof.

4. A compound of formula I as claimed in claim 1, in which:
R1 is phenyl,
   which is unsubstituted or substituted by 1 substituent from the group consisting of F, Cl, Br, I, CN and alkoxy having 1 or 2 carbon atoms;
R2 is phenyl,
   which is unsubstituted or substituted by 1 substituent from the group consisting of F, Cl, Br, I, CN and alkoxy having 1 or 2 carbon atoms;
R3 is $C_pH_{2p}$-R7;
   p is 0, 1, 2, 3;
R7 is $CH_3$, cycloalkyl having 3 or 4 carbon atoms or phenyl,
   where phenyl is unsubstituted or substituted by 1 or 2 substituents selected from the group consisting of F, Cl, Br, I, CN, alkyl having 1 or 2 carbon atoms and alkoxy having 1 or 2 carbon atoms;
R4 is hydrogen;
R5 is hydrogen;
R6 is hydrogen, F or alkyl having 1 or 2 carbon atoms;
X is CH;
or a pharmaceutically acceptable salt or trifluoroacetate thereof.

5. A compound of formula I as claimed in claim 1, selected from:
1R',2R'-1-(2-Cyclopropylmethoxy-1,2-diphenylethyl)-1H-pyridin-2-one,
1R',2S'-1-[2-Cyclopropylmethoxy-1-(4-fluorophenyl)-2-(4-methoxyphenyl)ethyl]-1H-pyridin-2-one,
1-(2-Cyclopropylmethoxy-1,2-diphenylethyl)-5-fluoro-1H-pyridin-2-one,
1R',2R'-5-Fluoro-1-(2-p-cyanophenoxy-1,2-di-p-fluorophenylethyl)-1H-pyridin-2-one,
1-[2-Cyclopropoxy-1,2-bis(4-fluorophenyl)ethyl]-5-fluoro-1H-pyridin-2-one,
1-[2-(4-Chlorophenyl)-2-cyclopropylmethoxy-1-phenylethyl]-1H-pyridin-2-one,
1R',2R'-1-[2-Cyclopropylmethoxy-1,2-bis(4-fluorophenyl)ethyl]-1H-pyridin-2-one,
1R',2S'-1-[2-Cyclopropylmethoxy-1,2-bis-(4-fluorophenyl)ethyl]-1H-pyridin-2-one,
1-[2-(4-Bromophenyl)-2-cyclopropylmethoxy-1-(4-fluorophenyl)ethyl]-1H-pyridin-2-one,
4-[1-Cyclopropylmethoxy-2-(4-fluorophenyl)-2-(2-oxo-2H-pyridin-1-yl)ethyl]benzonitrile, 1R',2R'-1-(2-Cyclopropylmethoxy-1,2-diphenylethyl)-5-fluoro-1H-pyridin-2-one, 1R',2R'-1-[1-(4-Fluorophenyl)-2-(4-methoxybenzyloxy)-2-(4-methoxyphenyl)ethyl]-1H-pyridin-2-one, 1-[2-Cyclopropylmethoxy-1,2-bis-(4-fluorophenyl)ethyl]-1H-pyridin-2-one, 4-[1-(4-Chlorophenyl)-2-(2-oxo-2H-pyridin-1-yl)-2-phenylethoxymethyl]benzonitrile, 1-[2-Cyclopropylmethoxy-1,2-bis-(4-fluorophenyl)ethyl]-5-fluoro-1H-pyridin-2-one, 1R',2R'-1-[2-Cyclopropylmethoxy-1-(4-fluorophenyl)-2-(4-methoxyphenyl)ethyl]-1H-pyridin-2-one and 1R',2S'-1-[1-(4-Fluorophenyl)-2-(4-methoxybenzyloxy)-2-(4-methoxyphenyl)ethyl]-1H-pyridin-2-one, or a pharmaceutically acceptable salt or trifluoroacetate thereof.

6. A pharmaceutical composition comprising a pharmaceutically effective amount of one or more compounds as claimed in claim 1 as active ingredient, together with one or more pharmaceutically acceptable carriers or additives.

* * * * *

UNITED STATES PATENT AND TRADEMARK OFFICE
CERTIFICATE OF CORRECTION

| | | |
|---|---|---|
| PATENT NO. | : 8,044,074 B2 | |
| APPLICATION NO. | : 11/954396 | |
| DATED | : October 25, 2011 | |
| INVENTOR(S) | : Joachim Brendel et al. | |

It is certified that error appears in the above-identified patent and that said Letters Patent is hereby corrected as shown below:

In column 2, line 21, delete "S," and insert -- S. --, therefor.

In column 10, line 2-9, delete " 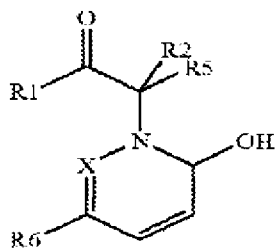 " and insert -- 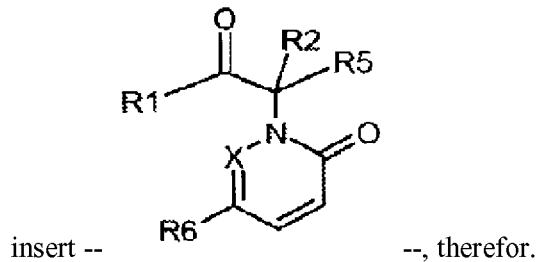 --, therefor.

In column 11, line 35, delete "VII," and insert -- VIII, --, therefor.

In column 18, line 19, delete "VII," and insert -- VIII, --, therefor.

In column 21, line 30, delete "diphenyl ethyl)-" and insert -- diphenylethyl)- --, therefor.

In column 23, line 33, delete "tetrabutyl-ammonium" and insert -- tetrabutylammonium --, therefor.

In column 31, line 9-10, delete "(ADinstruments," and insert -- (ADInstruments, --, therefor.

In column 31, line 33, delete "(ADinstruments," and insert -- (ADInstruments, --, therefor.

Signed and Sealed this
Seventh Day of February, 2012

David J. Kappos
*Director of the United States Patent and Trademark Office*

CERTIFICATE OF CORRECTION (continued)
U.S. Pat. No. 8,044,074 B2

In column 33, line 2, in claim 1, delete "4or" and insert -- 4 or --, therefor.